United States Patent [19]

Dewald et al.

[11] 4,104,315
[45] Aug. 1, 1978

[54] PROCESS FOR SEPARATING AN AR, AR-DIHALO-AR-ALKYLBENZENE FROM AN ISOMERIC MIXTURE OF AR, AR-DIHALO-AR-ALKYLBENZENES

[75] Inventors: James R. Dewald, Bay City, Mich.; Lowell D. Markley, Clayton, Calif.

[73] Assignee: The Dow Chemical Company, Midland, Mich.

[21] Appl. No.: 776,168

[22] Filed: Mar. 10, 1977

Related U.S. Application Data

[63] Continuation-in-part of Ser. No. 707,924, Jul. 22, 1976, Pat. No. 4,059,642.

[51] Int. Cl.$^2$ ............................................. C07C 25/04
[52] U.S. Cl. .................................................. 260/650 R
[58] Field of Search ................................... 260/650 R

[56] References Cited

PUBLICATIONS

Ohah et al., Aromatic Substitution XVIII, Friedel Crafts t–Butylation of Benzene and Methylbenzenes wt–Butyl Bromide & Isotulylene, JACS; 86, 3-20-64; p. 1060.

*Primary Examiner*—Delbert E. Gantz
*Assistant Examiner*—Joan Thierstein

[57] ABSTRACT

In a mixture of isomers of ar,ar-dihalo-ar-alkylbenzene wherein the halogen substituents are meta oriented with respect to each other, (e.g., a mixture of 3,5-dichlorocumene and 2,4-dichlorocumene), the 2,4-dihalo-1-alkylbenzene is preferentially reacted with an alkylating agent, e.g., an alkyl halide, by contacting the mixture with the agent in the presence of a Friedel-Crafts catalyst at a temperature of less than about 90° C. The resulting alkylated isomer is readily separated from the unreacted isomer(s) by simple distillation.

7 Claims, No Drawings

PROCESS FOR SEPARATING AN AR, AR-DIHALO-AR-ALKYLBENZENE FROM AN ISOMERIC MIXTURE OF AR, AR-DIHALO-AR-ALKYLBENZENES

CROSS REFERENCE TO RELATED APPLICATIONS

This application is a continuation-in-part of application Ser. No. 707,924 filed July 22, 1976 now U.S. Pat. No. 4,059,642.

BACKGROUND OF THE INVENTION

This invention relates to a process for separating one ar,ar-dihalo-ar-alkylbenzene from a mixture of ar,ar-dihalo-ar-alkylbenzenes.

Processes for the preparation of isomeric mixtures of ar,ar-dihalo-ar-alkylbenzenes are known in the art. For example, U.S. Pat. No. 2,186,960 to Dreisbach et al. discloses the preparation of polyisopropylhalobenzenes by reacting a halobenzene containing not more than four halo groups per benzene ring with an alkylating agent in the presence of a Friedel-Crafts catalyst such as aluminum trichloride.

Unfortunately, as taught in column 2, lines 19-26 of U.S. Pat. No. 2,186,960, the polyisopropyl halobenzenes are extremely difficult if not impossible to separate. Subsequent to the issuance of the aforementioned patent, it has been discovered that certain isomers of isopropyl halobenzenes are useful precursors in the manufacture of compounds exhibiting excellent biological activity.

In view of the severe difficulties existent in the conventional processes for preparing and separating such compounds from isomeric mixtures thereof, it would be highly desirable to provide an improved process for separating ar,ar-dihalo-ar-alkylbenzenes.

SUMMARY OF THE INVENTION

Accordingly, this invention is a process for separating ar,ar-dihalo-ar-alkylbenzenes wherein two substituents, preferably the halogen substituents, are meta oriented with respect to each other. For the purposes of this invention, the term ar,ar-dihalo-ar-alkylbenzene includes substituted benzenes wherein the alkyl substituent may be alkyl or substituted alkyl such as haloalkyl, aralkyl, alkoxyalkyl and the like. The process comprises contacting an isomeric mixture of ar,ar-dihalo-ar-alkylbenzenes with an alkylating or acylating agent in the presence of a Friedel-Crafts catalyst at a reaction temperature less than about 90° C such that the isomer having substituents in the 1,2,4- ring positions is preferentially alkylated or acylated. In the case of alkylation, the Friedel-Crafts catalyst is employed in catalytic amounts whereas in the acylation reaction, the Friedel-Crafts catalyst is employed in nearly stoichiometric amounts. The alkylated or acylated isomer is readily separated from the remaining unreacted isomers by simple distillation with the more volatile unreacted isomers constituting the lower boiling fraction.

The aforementioned preferential alkylation or acylation reaction is unique in that, at the particular temperature employed, usually less than about 5 mole percent of the 1,3,5- isomer is alkylated or acylated while essentially all of the 1,2,4- isomer is.

The ar,ar-dihalo-ar-alkylbenzenes as well as their acylated or alkylated products are useful precursors in the synthesis of other organic compounds. In addition, the ar,ar-dihalo-ar-alkylbenzenes are useful as organic solvents and as dielectric agents.

DETAILED DESCRIPTION OF THE INVENTION

In general, the isomeric mixture employed as a starting material in the practice of this invention contains at least two ar,ar-dihalo-ar-alkylbenzene isomers wherein at least one isomer has the halogen and alkyl or inertly substituted alkyl substituents in the 1,2,4-ring positions (hereinafter called a 1,2,4- isomer) and at least one other isomer has the halogen and alkyl or inertly substituted alkyl substituents in the 1,3,5-ring positions (hereinafter called a 1,3,5- isomer).

In preferred embodiments, the isomeric mixture contains 2,4-dihalo-1-alkylbenzene represented by formula I and 3,5-dihalo-1-alkylbenzene represented by formula II.

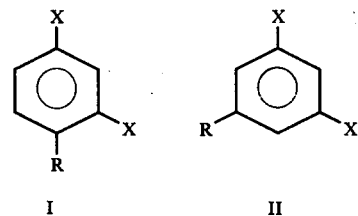

In the foregoing formulas, R is alkyl or inertly substituted alkyl such as haloalkyl, aralkyl, alkoxyalkyl and the like. Preferably R is alkyl having from 1 to 8 carbon atoms such as methyl, ethyl, propyl, butyl, hexyl and octyl, more preferably alkyl having 2 to 6 carbon atoms, most preferably isopropyl. Each X is individually a halogen, preferably chloro or bromo, most preferably chloro.

The isomeric mixture can be prepared in any of a number of ways. The preferred method is the alkylation of meta-dihalobenzene as by the method described in the parent application Ser. No. 707,924 filed July 22, 1976 now U.S. Pat. No. 4,059,642. The meta-dihalobenzene is readily obtained by an isomerization reaction wherein ortho- and/or para-dihalobenzenes are contacted with aluminum trichloride, e.g. by the method described in U.S. Pat. No. 2,819,321.

Suitable alkylating or acylating agents in the practice of this invention include conventional alkylating agents such as hydrocarbyl halides, e.g., alkyl halides or alkaryl halides; olefins; and alkyl alcohols and conventional acylating agents such as carboxylic acid halides. Alkylating agents which are capable of forming secondary carbonium ions but which do not normally form a tertiary carbonium ion are preferred.

Exemplary preferred alkylating agents include olefins such as propylene, 1- or 2-butene, 1- or 2-pentene and other similar linear olefins; linear alkyl halides such as isopropyl chloride, s-butyl bromide, 2- or 3-pentyl chloride and similar secondary alkyl halides; and alkaryl halides such as 2,4-dichloro-5-isopropylcumene, 2,4-dichloro-5-(s-butyl)cumene and others represented by the formula

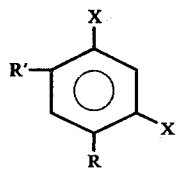

wherein X and R are as defined hereinbefore and R' is a linear alkyl group. Of the aforementioned preferred alkylating agents, those having 3–5 carbons are more preferred with the olefins being the most preferred.

Less preferred than the foregoing alkylating agents are the alcohols such as isopropyl alcohol, 1- or 2-butanol and other linear alcohols, particularly those having 3–5 carbons.

Suitable as acylating agents are the acid halides including acetyl chloride, propionyl chloride, butyryl chloride and others having 3 to about 5 carbon atoms and of the formula R"COX wherein R" is alkyl and X is halogen, preferably Cl. The acylating agents are not as preferred as the aforementioned alkylating agents because acyl groups are more difficult to remove from the benzene ring and the acylation reaction generally consumes much more than catalytic amounts of the Friedel-Crafts catalyst.

The alkylating or acylating agents are typically employed in the preferential reaction at a ratio of between about 0.1 to about 1 mole of agent per mole of the 1,2,4- isomer. In order to maintain the selectivity of the reaction, it is desirable to maintain the mole ratio of agent to reactant at less than one mole of agent per mole of the 1,2,4- isomer, preferably from about 0.3 to about 0.5, most preferably 0.3 mole of agent per mole of the 1,2,4- isomer.

Catalysts suitably employed in the practice of this invention are generally Friedel-Crafts catalysts such as aluminum trihalide, e.g., aluminum trichloride and aluminum tribromide, sulfuric acid, boron trifluoride, ferric chloride, stannic chloride, titanium tetrachloride, phosphorus pentachloride, antimony trichloride. Of the foregoing, the aluminum trihalides are preferred, with aluminum trichloride being most preferred.

In preparation for the preferential reaction, a formulation is formed of the catalyst and the isomeric mixture. The formulation is agitated sufficiently to keep the catalyst thoroughly dispersed throughout the formulation, e.g., by stirring, before and during the reaction. For the alkylation reaction, the catalyst should be present in a catalytic amount. Preferably such a catalytic amount is from about one to about ten weight percent, most preferably from about two to about five weight percent, based on the isomeric mixture. For the acylation reaction nearly stoichiometric amounts of the Friedel-Crafts catalyst is required.

Advantageously, after the catalyst and isomeric mixture are combined, the alkylating or acylating agent is added in metered amounts to the mixture of catalyst and isomers in order to control the heat of reaction as the substitution product is formed. During the reaction, the reaction mixture should be maintained at a temperature below about 90° C, advantageously at a temperature of between about −20° C and about 60° C, and preferably between about −20° C and about 20° C. While reaction pressure is not critical, pressures between about 0 psig and about 25 psig while venting the reactor are advantageously employed. To assure complete reaction, the mixture is stirred for a period of time sufficient to assure complete reaction. Upon completion of the reaction, a quantity of water sufficient to destroy any residual catalyst is added.

The reaction product (alkylated or acylated) is then separated from the reacted isomers. Although not critical, this separation is typically accomplished by simple distillation of the lower boiling unreacted isomers from the higher boiling reacted isomers.

The following example is given to illustrate the invention and should not be construed as limiting its scope. All percentages in the example are by weight unless otherwise indicated.

EXAMPLE

An isomeric mixture (231 parts) of 45 percent 2,4-dichlorocumene (a 1,2,4- isomer) and 55 percent 3,5-dichlorocumene (a 1,3,5- isomer) is prepared by Example 1 of the parent application. This isomeric mixture is stirred with 2.5 parts anhydrous aluminum chloride at 25° C–40° C for 20 minutes in a liter three-necked flask equipped with cooling means, a thermometer, a graduated dropping funnel, a stirrer and dry ice condenser. A 48-part portion of isopropyl chloride is then added dropwise over a period of 1 hour to the aforementioned mixture while stirring the mixture and maintaining the temperature of the reaction mixture at 25° C–40° C. The mixture is stirred at 25° C–40° C for an additional half hour and 40 parts of water is added to destroy the catalyst. The resulting mixture, which is allowed to stand for 1–2 hours without agitation, separates into two layers. The lower product layer is then recovered and distilled, using a 10-plate column and a pressure of 10–40 mm Hg. A 115-part portion of 3,5-dichlorocumene (b.p. 119° C/25 mm Hg), is recovered as the overhead product. This recovery of product represents a 90.5 percent yield based on available 3,5-dichlorocumene. Analysis of the recovered distillate indicates a constituency as follows:

94–98 percent 3,5-dichlorocumene
1–3 percent 2,4-dichlorocumene
1–3 percent 2,4-dichloro-5-isopropylcumene
0.5 percent unknown.

Analysis of the remaining pot residue from the aforementioned distillation indicates 142 parts of a mixture of 91.5 percent 2,4-dichloro-5-isopropylcumene and 8.5 percent 3,5-dichlorocumene.

As evidenced by the foregoing results, essentially all of the 2,4-dichlorocumene alkylates whereas very little of the 3,5-dichlorocumene does, thus illustrating the preferential alkylation characteristics of the novel process disclosed herein.

Similar results are obtained if propene is substituted for the isopropyl chloride in the foregoing procedure.

What is claimed is:

1. A process for separating ar,ar-dihalo-ar-alkylbenzenes wherein two of the ring substituents are meta oriented with respect to each other and wherein alkyl includes substituted alkyl, said process comprising (1) contacting an isomeric mixture containing an ar,ar-dihalo-ar-alkylbenzene having the substituents in the 1,2,4- ring positions (1,2,4- isomer) and an isomer thereof having the substituents in the 1,3,5-ring positions (1,3,5- isomer) with an alkylating agent in the presence of a catalytic amount of a Friedel-Crafts catalyst at a reaction temperature less than about 90° C such that the 1,2,4- isomer is preferentially alkylated and (2)

separating the alkylated 1,2,4- isomer from the unreacted 1,3,5- isomer.

2. The process of claim 1 wherein (1) the isomeric mixture contains ar,ar-dihalo-ar-alkylbenzenes represented by the formulas:

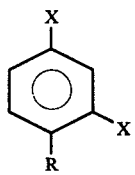 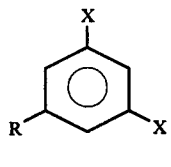

1,2,4-isomer        1,3,5-isomer wherein each X is individually halogen and R is alkyl or substituted alkyl and (2) the isomeric mixture is contacted with an alkylating agent in the presence of a catalytic amount of an aluminum trihalide at a reaction temperature of between about $-20°$ C and about 60° C.

3. The process of claim 2 wherein X is Cl or Br and R is alkyl having from 3 to 5 carbon atoms.

4. The process of claim 3 wherein R contains three carbon atoms.

5. The process of claim 2 wherein the alkylating agent is an alkyl halide or an olefin.

6. The process of claim 2 wherein the alkylating agent is isopropyl chloride or propene.

7. The process of claim 2 wherein an isomeric mixture of 3,5-dichlorocumene and 2,4-dichlorocumene is contacted with propene or isopropyl chloride in the presence of from about 0.5 to about 1.5 weight percent of aluminum trichloride at a temperature between about $-20°$ C and about 20° C.

* * * * *